(12) United States Patent
Heuser et al.

(10) Patent No.: US 8,062,321 B2
(45) Date of Patent: Nov. 22, 2011

(54) CATHETER SYSTEM FOR CONNECTING ADJACENT BLOOD VESSELS

(75) Inventors: Richard R. Heuser, Phoenix, AZ (US); James D. Joye, Saratoga, CA (US)

(73) Assignees: PQ Bypass, Inc.; Saratoga, Inc.

( * ) Notice: Subject to any disclaimer, the term of this patent is extended or adjusted under 35 U.S.C. 154(b) by 624 days.

(21) Appl. No.: 11/735,382

(22) Filed: Apr. 13, 2007

(65) Prior Publication Data
US 2008/0065019 A1    Mar. 13, 2008

Related U.S. Application Data

(63) Continuation-in-part of application No. 11/340,324, filed on Jan. 25, 2006, now Pat. No. 7,374,567.

(60) Provisional application No. 60/887,277, filed on Jan. 30, 2007.

(51) Int. Cl.
  *A61B 17/34* (2006.01)
(52) U.S. Cl. ........................................ 606/185
(58) Field of Classification Search .............. 606/153, 606/170, 183, 167, 181, 185, 189, 194, 198, 606/219, 200, 213–215; 604/95.01, 104, 604/164.01; 623/1.1, 1.11–1.15, 1.2, 1.23, 623/1.35, 1.36
See application file for complete search history.

(56) References Cited

U.S. PATENT DOCUMENTS

| | | |
|---|---|---|
| 2,729,211 A | 1/1956 | Peter |
| 3,751,305 A | 8/1973 | Huebscher |
| 3,788,318 A | 1/1974 | Kim et al. |
| 3,828,770 A | 8/1974 | Kuris et al. |
| 3,828,782 A | 8/1974 | Polin |
| 4,000,739 A | 1/1977 | Stevens |
| 4,241,289 A | 12/1980 | Bowling |
| 4,430,081 A | 2/1984 | Timmermans |

(Continued)

FOREIGN PATENT DOCUMENTS

EP    0696447    2/1996

(Continued)

OTHER PUBLICATIONS

Heuser, M.D., Richard R., et al. "The Use of a New Wire in a 6-Year-Old Coronary Artery Occlusion: The Jagwire Recanalization Guidewire." Catheterization and Cardiovascular Diagnosis. 1993. pp. 173-176. vol. 29.

(Continued)

*Primary Examiner* — S. Thomas Hughes
*Assistant Examiner* — Katherine M Shi
(74) *Attorney, Agent, or Firm* — Wilson Sonsini Goodrich & Rosati

(57) ABSTRACT

The catheter apparatus may be used to assist in creating a fistula between two adjacent blood vessels. The apparatus includes a catheter for inserting into a first blood vessel which lies adjacent to a second blood vessel, the catheter having a plurality of openings through which a physician may navigate a piercing tool. The physician maneuvers the tip of the catheter to a position within the first blood vessel adjacent to a portion of the first blood vessel wall in which the physician intends to create an opening. The physician may then rotate the piercing tool within the catheter and extend the piercing tool through one opening at a time, without rotating the catheter, until the physician chooses an opening that is properly aimed at the second blood vessel. Such a configuration allows for a wide arc of potential firing space.

24 Claims, 7 Drawing Sheets

U.S. PATENT DOCUMENTS

| | | | |
|---|---|---|---|
| 4,445,892 A | 5/1984 | Hussein et al. | |
| 4,590,669 A | 5/1986 | Imamura | |
| 4,634,432 A | 1/1987 | Kocak | |
| 4,637,814 A | 1/1987 | Leiboff | |
| 4,650,466 A | 3/1987 | Luther | |
| 4,650,472 A | 3/1987 | Bates | |
| 4,682,981 A | 7/1987 | Suzuki et al. | |
| 4,705,511 A | 11/1987 | Kocak | |
| 4,706,671 A | 11/1987 | Weinrib | |
| 4,744,364 A | 5/1988 | Kensey | |
| 4,771,777 A | 9/1988 | Horzewski et al. | |
| 4,772,258 A | 9/1988 | Marangoni et al. | |
| 4,796,640 A | 1/1989 | Webler | |
| 4,832,688 A | 5/1989 | Sagae et al. | |
| 4,862,891 A | 9/1989 | Smith | |
| 4,874,378 A | 10/1989 | Hillstead | |
| 4,883,460 A | 11/1989 | Zanetti | |
| 4,895,564 A | 1/1990 | Farrell | |
| 4,911,163 A | 3/1990 | Fina | |
| 4,950,257 A | 8/1990 | Hibbs et al. | |
| 4,994,071 A | 2/1991 | MacGregor | |
| 5,078,684 A | 1/1992 | Yasuda | |
| 5,092,846 A | 3/1992 | Nishijima et al. | |
| 5,112,310 A | 5/1992 | Grobe | |
| 5,147,336 A | 9/1992 | Wendell et al. | |
| 5,163,906 A | 11/1992 | Ahmadi | |
| 5,176,144 A | 1/1993 | Yoshikoshi et al. | |
| 5,183,470 A | 2/1993 | Wettermann | |
| 5,199,939 A | 4/1993 | Dake et al. | |
| 5,207,228 A | 5/1993 | Roelandt et al. | |
| 5,213,417 A | 5/1993 | Yamada et al. | |
| 5,217,019 A | 6/1993 | Hughes | |
| 5,217,484 A | 6/1993 | Marks | |
| 5,234,437 A | 8/1993 | Sepetka | |
| 5,242,410 A | 9/1993 | Melker | |
| 5,256,141 A | 10/1993 | Gencheff et al. | |
| 5,256,146 A * | 10/1993 | Ensminger et al. | 604/104 |
| 5,256,158 A | 10/1993 | Tolkoff et al. | |
| 5,257,979 A | 11/1993 | Jagpal | |
| 5,261,878 A | 11/1993 | Galindo | |
| 5,267,966 A | 12/1993 | Paul | |
| 5,275,488 A | 1/1994 | Stelts | |
| 5,281,793 A | 1/1994 | Gavin et al. | |
| 5,290,310 A | 3/1994 | Makower et al. | |
| 5,292,311 A | 3/1994 | Cope | |
| 5,320,617 A | 6/1994 | Leach | |
| 5,330,486 A | 7/1994 | Wilk | |
| 5,354,271 A | 10/1994 | Voda | |
| 5,356,486 A | 10/1994 | Sugarman et al. | |
| 5,364,392 A | 11/1994 | Warner et al. | |
| 5,370,459 A | 12/1994 | Culbertson et al. | |
| 5,380,304 A | 1/1995 | Parker | |
| 5,395,341 A | 3/1995 | Slater | |
| 5,403,341 A | 4/1995 | Solar | |
| 5,415,635 A | 5/1995 | Bagaoisan et al. | |
| 5,423,774 A | 6/1995 | Fischell et al. | |
| 5,437,292 A | 8/1995 | Kipshidze et al. | |
| 5,439,446 A | 8/1995 | Barry | |
| 5,443,478 A | 8/1995 | Purdy | |
| 5,445,646 A | 8/1995 | Euteneuer et al. | |
| 5,458,573 A | 10/1995 | Summers | |
| 5,462,359 A | 10/1995 | Reichl et al. | |
| 5,462,529 A | 10/1995 | Simpson et al. | |
| 5,466,230 A | 11/1995 | Davila | |
| 5,499,975 A | 3/1996 | Cope et al. | |
| 5,512,291 A | 4/1996 | Li | |
| 5,514,236 A | 5/1996 | Avellanet et al. | |
| 5,545,193 A | 8/1996 | Fleischman et al. | |
| 5,545,209 A | 8/1996 | Roberts et al. | |
| 5,549,626 A | 8/1996 | Miller et al. | |
| 5,578,008 A | 11/1996 | Hara | |
| 5,591,137 A | 1/1997 | Stevens | |
| 5,591,206 A | 1/1997 | Moufarrege | |
| 5,599,325 A | 2/1997 | Ju et al. | |
| 5,620,457 A | 4/1997 | Pinchasik et al. | |
| 5,628,786 A | 5/1997 | Banas et al. | |
| 5,632,760 A | 5/1997 | Sheiban et al. | |
| 5,632,762 A | 5/1997 | Myler | |
| 5,645,560 A | 7/1997 | Crocker et al. | |
| 5,660,473 A | 8/1997 | Noma et al. | |
| 5,665,107 A | 9/1997 | Hammerslag | |
| 5,667,523 A | 9/1997 | Bynon et al. | |
| 5,674,241 A | 10/1997 | Bley et al. | |
| 5,681,295 A | 10/1997 | Gyure et al. | |
| 5,683,453 A | 11/1997 | Palmaz | |
| 5,688,266 A | 11/1997 | Edwards et al. | |
| 5,695,498 A | 12/1997 | Tower | |
| 5,707,359 A | 1/1998 | Bufalini | |
| 5,725,524 A | 3/1998 | Mulier et al. | |
| 5,725,572 A | 3/1998 | Lam et al. | |
| 5,728,068 A | 3/1998 | Leone et al. | |
| 5,733,044 A | 3/1998 | Rose et al. | |
| 5,733,267 A | 3/1998 | Del Toro | |
| 5,735,892 A | 4/1998 | Myers et al. | |
| 5,743,900 A | 4/1998 | Hara | |
| 5,749,880 A | 5/1998 | Banas et al. | |
| 5,762,630 A | 6/1998 | Bley et al. | |
| 5,769,077 A | 6/1998 | Lindegren | |
| 5,792,070 A | 8/1998 | Kauphusman et al. | |
| 5,800,393 A | 9/1998 | Sahota | |
| 5,800,520 A | 9/1998 | Fogarty et al. | |
| 5,807,350 A | 9/1998 | Diaz | |
| 5,814,016 A | 9/1998 | Valley et al. | |
| 5,814,064 A | 9/1998 | Daniel et al. | |
| 5,820,607 A | 10/1998 | Tcholakian et al. | |
| 5,830,222 A | 11/1998 | Makower | |
| 5,830,224 A | 11/1998 | Cohn et al. | |
| 5,833,644 A | 11/1998 | Zadno-Azizi et al. | |
| 5,833,650 A | 11/1998 | Imran | |
| 5,843,124 A | 12/1998 | Hammerslag | |
| 5,843,166 A | 12/1998 | Lentz et al. | |
| 5,853,409 A | 12/1998 | Swanson et al. | |
| 5,855,563 A | 1/1999 | Kaplan et al. | |
| 5,857,998 A | 1/1999 | Barry | |
| 5,868,705 A | 2/1999 | Bagaoisan et al. | |
| 5,868,708 A | 2/1999 | Hart et al. | |
| 5,893,867 A | 4/1999 | Bagaoisan et al. | |
| 5,897,497 A | 4/1999 | Fernandez | |
| 5,899,917 A | 5/1999 | Edwards et al. | |
| 5,906,636 A | 5/1999 | Casscells, III et al. | |
| 5,911,710 A | 6/1999 | Barry et al. | |
| 5,916,264 A | 6/1999 | Von Oepen et al. | |
| 5,928,260 A | 7/1999 | Chin et al. | |
| 5,928,279 A | 7/1999 | Shannon et al. | |
| 5,935,075 A | 8/1999 | Casscells et al. | |
| 5,938,694 A | 8/1999 | Jaraczewski et al. | |
| 5,944,019 A | 8/1999 | Knudson et al. | |
| 5,957,961 A | 9/1999 | Maguire et al. | |
| 5,964,798 A | 10/1999 | Imran | |
| 5,968,064 A | 10/1999 | Selmon et al. | |
| 5,976,178 A | 11/1999 | Goldsteen et al. | |
| 5,980,532 A | 11/1999 | Wang | |
| 5,984,955 A | 11/1999 | Wisselink | |
| 5,989,223 A | 11/1999 | Chu et al. | |
| 5,997,526 A | 12/1999 | Giba et al. | |
| 6,004,310 A | 12/1999 | Bardsley et al. | |
| 6,013,085 A | 1/2000 | Howard | |
| 6,017,365 A | 1/2000 | Von Oepen | |
| 6,019,779 A | 2/2000 | Thorud et al. | |
| 6,022,336 A | 2/2000 | Zadno-Azizi et al. | |
| 6,022,343 A | 2/2000 | Johnson et al. | |
| 6,030,406 A | 2/2000 | Davis et al. | |
| 6,033,434 A | 3/2000 | Borghi | |
| 6,064,902 A | 5/2000 | Haissaguerre et al. | |
| 6,068,656 A | 5/2000 | Von Oepen | |
| 6,071,292 A | 6/2000 | Makower et al. | |
| 6,120,534 A | 9/2000 | Ruiz | |
| 6,124,523 A | 9/2000 | Banas et al. | |
| 6,156,064 A | 12/2000 | Chouinard | |
| 6,159,197 A | 12/2000 | Heuser | |
| 6,168,579 B1 | 1/2001 | Tsugita | |
| 6,176,872 B1 | 1/2001 | Miksza | |
| 6,187,033 B1 | 2/2001 | Schmitt et al. | |
| 6,190,353 B1 | 2/2001 | Makower et al. | |
| 6,193,747 B1 | 2/2001 | Von Oepen | |
| 6,231,587 B1 | 5/2001 | Makower | |
| 6,245,052 B1 | 6/2001 | Orth et al. | |

| | | |
|---|---|---|
| 6,264,685 B1 | 7/2001 | Ahari |
| 6,264,690 B1 | 7/2001 | Von Oepen |
| 6,283,958 B1 | 9/2001 | Vogl et al. |
| 6,308,090 B1 | 10/2001 | Tu et al. |
| 6,325,826 B1 | 12/2001 | Vardi et al. |
| 6,364,900 B1 | 4/2002 | Heuser |
| 6,383,214 B1 | 5/2002 | Banas et al. |
| 6,408,214 B1 | 6/2002 | Williams et al. |
| 6,464,665 B1 | 10/2002 | Heuser |
| 6,464,681 B1 | 10/2002 | Heuser |
| 6,475,226 B1 | 11/2002 | Belef et al. |
| 6,530,914 B1 | 3/2003 | Mickley |
| 6,536,949 B1 | 3/2003 | Heuser |
| 6,582,394 B1 | 6/2003 | Reiss et al. |
| 6,613,078 B1 | 9/2003 | Barone |
| 6,638,268 B2 | 10/2003 | Niazi |
| 6,709,455 B1 | 3/2004 | Chouinard |
| 6,726,677 B1 | 4/2004 | Flaherty et al. |
| 6,746,479 B2 | 6/2004 | Ehr et al. |
| 6,830,568 B1 | 12/2004 | Kesten et al. |
| 6,858,038 B2 | 2/2005 | Heuser |
| 6,863,684 B2 | 3/2005 | Kim et al. |
| 6,866,805 B2 | 3/2005 | Hong et al. |
| 6,929,009 B2 | 8/2005 | Makower et al. |
| 6,987,660 B2 | 1/2006 | Stevenson et al. |
| 7,056,325 B1 | 6/2006 | Makower et al. |
| 7,059,330 B1 | 6/2006 | Makower et al. |
| 7,094,230 B2 | 8/2006 | Flaherty et al. |
| 7,134,438 B2 | 11/2006 | Makower et al. |
| 7,159,592 B1 | 1/2007 | Makower et al. |
| 7,166,088 B2 | 1/2007 | Heuser |
| 7,179,250 B2 | 2/2007 | Heuser |
| 7,179,270 B2 | 2/2007 | Makower |
| 7,191,015 B2 | 3/2007 | Lamson et al. |
| 7,300,459 B2 | 11/2007 | Heuser |
| 2001/0003161 A1 | 6/2001 | Vardi et al. |
| 2001/0049549 A1 | 12/2001 | Boylan et al. |
| 2002/0052643 A1 | 5/2002 | Wholey et al. |
| 2002/0178570 A1 | 12/2002 | Sogard et al. |
| 2002/0179098 A1 | 12/2002 | Makower et al. |
| 2003/0055402 A1 | 3/2003 | Zhou |
| 2003/0055484 A1 | 3/2003 | Lau et al. |
| 2003/0093029 A1* | 5/2003 | McGuckin et al. ............ 604/43 |
| 2003/0130598 A1 | 7/2003 | Manning et al. |
| 2003/0139797 A1 | 7/2003 | Johnson et al. |
| 2003/0163156 A1 | 8/2003 | Herbert |
| 2003/0199967 A1 | 10/2003 | Hartley et al. |
| 2003/0212450 A1 | 11/2003 | Schlick |
| 2004/0019373 A1 | 1/2004 | Casey et al. |
| 2004/0082989 A1 | 4/2004 | Cook et al. |
| 2004/0098095 A1 | 5/2004 | Burnside et al. |
| 2004/0106978 A1 | 6/2004 | Greenberg et al. |
| 2004/0116831 A1 | 6/2004 | Vrba |
| 2004/0162603 A1 | 8/2004 | Golds et al. |
| 2004/0167607 A1 | 8/2004 | Frantzen |
| 2004/0225305 A1* | 11/2004 | Ewers et al. ................. 606/153 |
| 2005/0125011 A1 | 6/2005 | Spence et al. |
| 2005/0182480 A1 | 8/2005 | Doran et al. |
| 2006/0047222 A1 | 3/2006 | Heuser |
| 2006/0122685 A1 | 6/2006 | Bonsignore et al. |
| 2006/0217799 A1 | 9/2006 | Mailander et al. |
| 2006/0229638 A1 | 10/2006 | Abrams et al. |
| 2007/0021730 A1 | 1/2007 | Flaherty et al. |
| 2007/0083257 A1 | 4/2007 | Pal et al. |
| 2007/0156231 A1 | 7/2007 | Weber |
| 2007/0208370 A1* | 9/2007 | Hauser et al. ................. 606/200 |
| 2007/0282429 A1* | 12/2007 | Hauser et al. ................ 623/1.16 |
| 2008/0009804 A1* | 1/2008 | Rosetti .......................... 604/173 |

FOREIGN PATENT DOCUMENTS

| | | |
|---|---|---|
| EP | 0707864 | 4/1996 |
| EP | 0819411 | 1/1998 |
| EP | 0917886 | 5/1999 |
| EP | 1421970 | 5/2004 |
| FR | 2753907 | 3/1998 |
| JP | 0003094773 | 4/1991 |
| WO | WO9214406 | 9/1992 |
| WO | WO9640348 | 12/1996 |
| WO | WO9717101 | 5/1997 |
| WO | WO9800090 | 1/1998 |
| WO | WO9811933 | 3/1998 |
| WO | WO9819632 | 5/1998 |
| WO | WO9826731 | 6/1998 |
| WO | WO9839047 | 9/1998 |
| WO | WO9908744 | 2/1999 |
| WO | WO9913808 | 3/1999 |
| WO | WO9924105 | 5/1999 |
| WO | WO9934749 | 7/1999 |
| WO | WO9936002 | 7/1999 |
| WO | WO0166038 | 3/2001 |
| WO | WO2005096995 | 10/2005 |

OTHER PUBLICATIONS

Baffour, M.S.C., R. et al. "An Angiographic Study of Ischemia as a Determinant of Neovascularization in Arteriovenous Reversal." Surgery, Gynecology & Obstetrics. Jan. 1988. pp. 28-32. vol. 166.

Bernheim, M.D., Bertram. "Arteriovenous Anastomosis—Reversal of the Circulation—as a Preventative of Gangrene of the Extremeties." Arteriovenous Anastomosis. Undated.

Blaisdell, M.D., William, et al. "Revascularization of Severely Ischemic Extremeties with an Arteriovenous Fistula." American Journal of Surgery. Aug. 1966. pp. 166-174. vol. 112.

Cuttino Jr., John, et al. "Collateral Vessel Formation: Isolation of a Transferrable Factor Promoting a Vascular Response." Basic Research in Cardiology. Jan. 9, 1975. pp. 568-573. vol. 70, No. 5.

Elsner, M.D., Mathias, et al. "Coronary Stent Grafts Covered by a Polytetrafluoroethylene Membrane." The American Journal of Cardiology. Aug. 1, 1999. pp. 335-338. vol. 84.

Gerard, M.D., Dava, et al. "Acute Physiologic Effects of Arteriovenous Anastomosis and Fistula in Revascularizing the Ischemic Canine Hind Limb." Surgery. Apr. 1981. pp. 485-493. vol. 89, No. 4.

Goldsmith, M.D., Harry, et al. "Lipid Angiogenic Factor from Omentum." JAMA. Oct. 19, 1984. pp. 2034-2036. vol. 252, No. 15.

Halstead, M.D., Albert. "Arteriovenous Anastomosis in the Treatment of Gangrene in the Extremeties." Surgery, Gynecology and Obstetrics. 1912. pp. 1-19. vol. 16.

Howell, M.D., Marcus, et al. "Preliminary Results of Endovascular Abdominal Aortic Aneurysm Exclusion with the AneuRx Stent-Graft." Journal of the American College of Cardiology. 2001. pp. 1040-1048. vol. 38, No. 4.

Kumar, S., et al. "Angiogenesis Factor from Human Myocardial Infarcts." The Lancet. Aug. 13, 1983. pp. 364-368.

Matolo, M.D., Nathaniel. "Use of an Arteriovenous Fistula for Treatement of the Severely Ischemic Extremity: Experimental Evaluation." Ann. Surg. Nov. 1976. pp. 622-625. vol. 184, No. 5.

Oesterle, et al. "An Embolization Containment Device." Catheterization and Cardiovascular Interventions. 1999. pp. 243-250. vol. 47.

Robertson, M.D., Roy, et al. "Collateral Circulation in the Presence of Experimental Arteriovenous Fistula." Surgery. Jan. 1950. pp. 1-16. vol. 27, No. 1.

Root, M.D., Harlan, et al. "Effects of an Arteriovenous Fistula on the Devascularized Limb." JAMA. Feb. 22, 1965. pp. 109-112. vol. 191, No. 8.

Sheil, A.G.R. "Treatment of Critical Ischaemia of the Lower Limb by Venous Arterialization: an Interim Report." Br. J. Surg. 1977. pp. 197-199.

Szilagyi, M.D., Emerick. "Femoral Arteriovenous Anastomosis in the Treatment of Occlusive Arterial Disease." A.M.A. Archives of Surgery. Undated.

English Abstract of JP0003094773 of Inaba et al.

English Abstract FR2753907 of Boussignac et al., from WO/98/14233 publication, from, which FR2753907 claims priority.

Kalmar, M.D., Gabor, et al. "Radial Force and Wall Apposition of Balloon-expandable Vascular Stents in Eccentric Stenoses: An In Vitro Evaluation in a Curved Vessel Model." Journal of Vascular and Interventional Radiology. May 2002. pp. 499-508. vol. 13, No. 5.

Johnson & Johnson Gateway, LLC. "Chronic Total Occlusion (CTO) Technologies." http://www.jnjgateway.com/home.jhtml?loc=USENG&page=viewContent&contentId=09008b9881163810&parentId=09008b9881163810. 2007. Printed Jan. 17, 2007.

Rossi, Anne V. "510(k) Summary per 21 CFR 807.92 re BSC IQ Hydrophilic Guide Wire and Response Letter from Department of Health & Human Services." Aug. 1, 2003.

Terumo Medical Corporation. "Glidewire Hydrophilic Coated Guidewire Designed for Peripheral Applications." http://www.terumomedical.com/SubDepts.asp?myID=79. 2002. Printed Jan. 30, 2007.

Heuser, M.D., Richard R., et al. "Endoluminal Grafting for Percutaneous Aneurysm Exclusion in an Aortocoronary Saphenous Vein Graft: The First Clinical Experience." Journal of Endovascular Surgery. 1995. pp. 81-88. vol. 2.

* cited by examiner

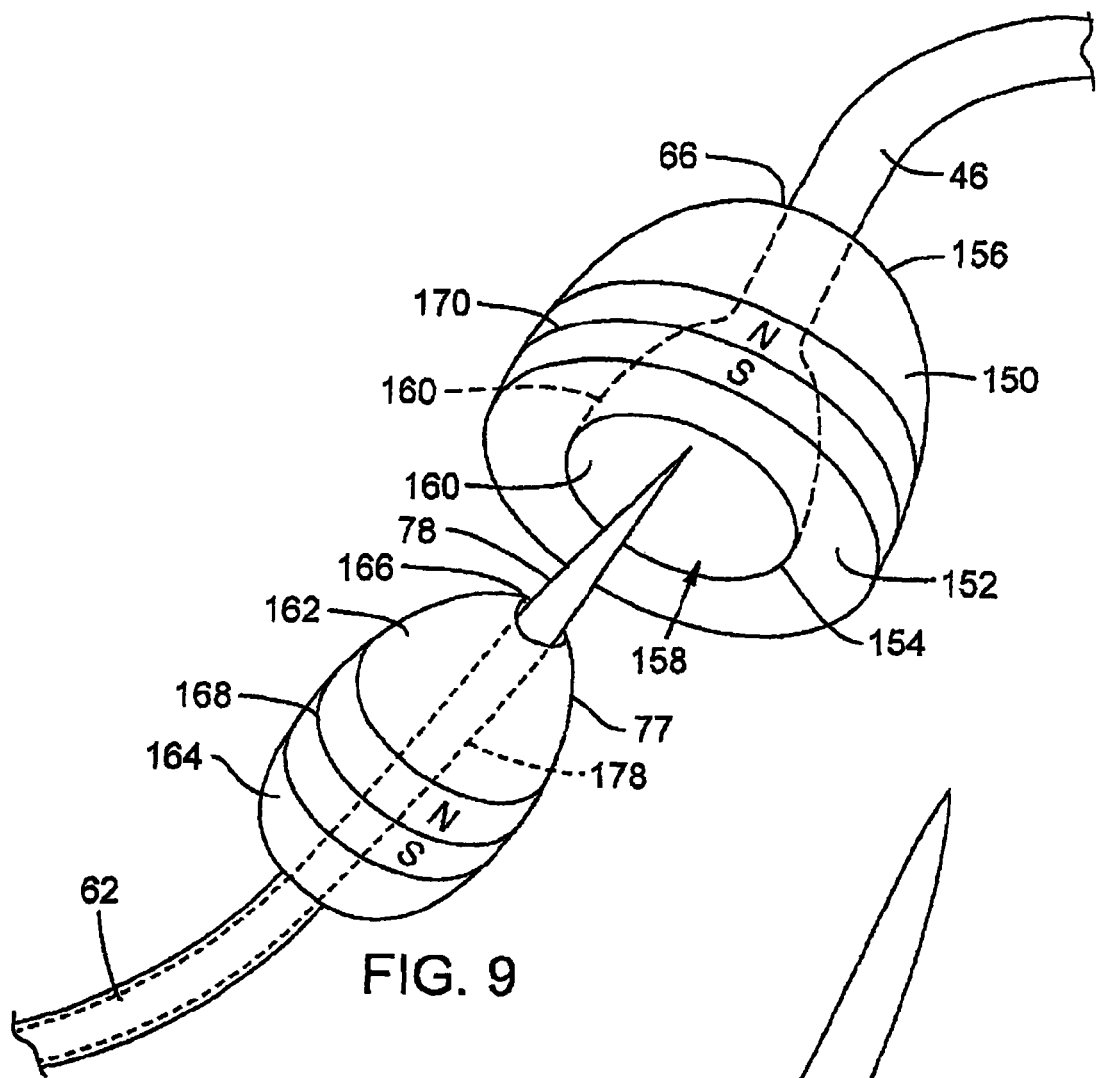
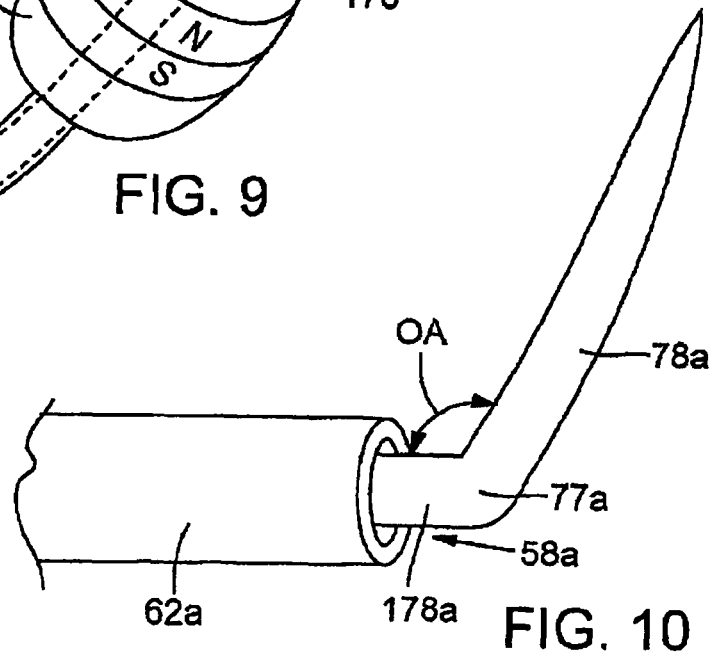
FIG. 9
FIG. 10

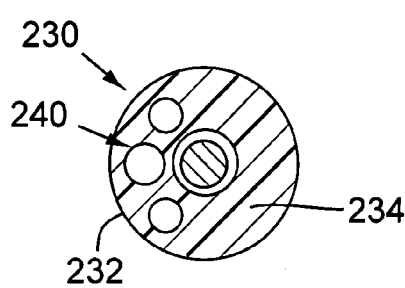
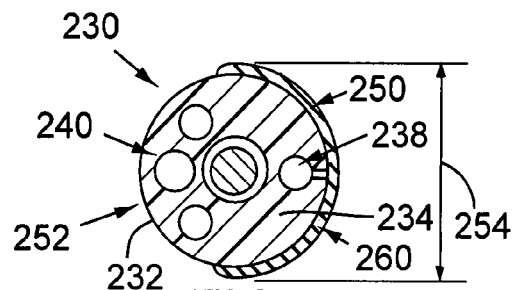
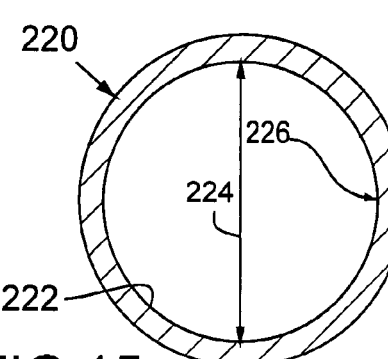
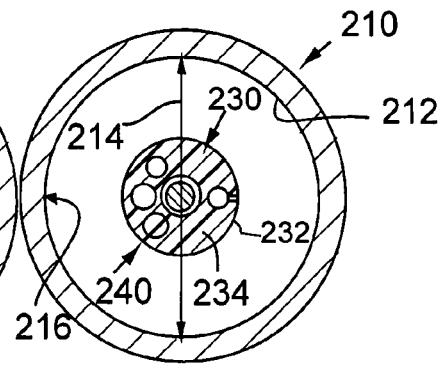
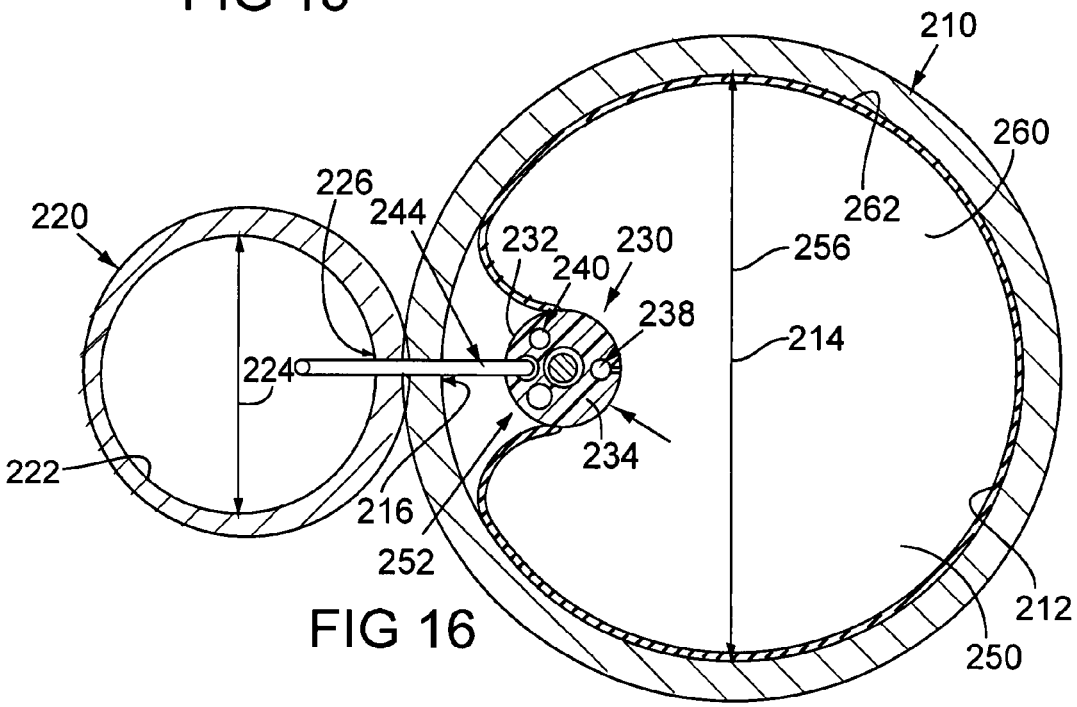

CATHETER SYSTEM FOR CONNECTING ADJACENT BLOOD VESSELS

CROSS REFERENCE TO RELATED APPLICATIONS

This application is a continuation-in-part of application Ser. No. 11/340,324, filed Jan. 25, 2006, now U.S. Pat. No. 7,374,567 B2, which claims the benefit of Provisional Application Ser. No. 60/887,277, filed on Jan. 30, 2007, the full disclosures of which are incorporated by reference.

BACKGROUND

This disclosure relates generally to a catheter system for connecting adjacent blood vessels, e.g, an artery and an adjacent vein to adapt the vein for arterial blood flow. More particularly the invention concerns a system of two catheters with mating, magnetic tips for creating openings in the artery wall and vein wall to form a fistula connecting the blood vessels. Further, the disclosure relates to a ratchetable catheter having a wide arc of potential space through which a piercing tool may be fired from a first blood vessel to a second blood vessel.

A catheter apparatus and method for arterializing a section of a vein to bypass a clogged artery are shown in U.S. Pat. No. 6,464,665, which is hereby incorporated by reference. The method is used to bypass a stenosis in the artery that obstructs blood flow in a portion of the artery. If the obstructed portion of the artery can be bypassed, blood flow will be restored downstream from the stenosis. A vein running alongside the artery in the obstructed portion of the artery can be used for the bypass.

The catheter apparatus includes one catheter for inserting into the artery and another catheter for inserting into the adjacent vein. The physician maneuvers the tips of both catheters to coincident positions within each blood vessel adjacent one end of the obstructed portion of the artery. The physician then creates an opening from the inside of one blood vessel through the vessel wall and then through the wall of the other blood vessel.

An issue arises in co-locating the openings in the two blood vessels and holding the vessel walls in place to ensure that a channel will be created between the vessels so that blood will flow from one vessel to the other. A further issue arises in aiming and maintaining the position of the catheters inside the vessels. In particular, veins often have diameters much larger than arteries, making hitting a smaller artery from a larger vein difficult. Additionally, larger veins often allow a catheter too much freedom of movement inside the vein.

SUMMARY OF THE INVENTION

The disclosed system and method provides for creating paired, co-located openings and a consequent fistula between an artery and an adjacent vein to bypass an arterial blockage. The system includes a piercing tool on a first catheter that mates with a receptor on a second catheter to create the co-located openings at one side of the blockage. Magnets incorporated in either or both catheters may be used to draw the piercing tool into the receptor. The piercing tool and receptor typically are provided with complementary, mating contours to draw the piercing tool sufficiently into the receptor to ensure completion of the openings. The openings may be expanded by balloon angioplasty and a stent is typically then installed to interconnect the openings to ensure a fistula is established between the vessels. The process may be repeated at the other side of the arterial blockage to complete the bypass.

Another aspect of the disclosure provides for a plurality of openings that may be used to assist in creating a fistula between two adjacent blood vessels. The apparatus includes a catheter for inserting into a first blood vessel which lies adjacent to a second blood vessel, the catheter having a plurality of openings through which a physician may navigate a piercing tool. The physician maneuvers the tip of the catheter to a position within the first blood vessel adjacent to a portion of the first blood vessel wall in which the physician intends to create an opening. The physician may then rotate the piercing tool within the catheter and extend the piercing tool through one opening at a time, without rotating the catheter, until the physician chooses an opening that is properly aimed at the second blood vessel.

BRIEF DESCRIPTION OF THE DRAWINGS

FIG. 9 is a close-up perspective view of the mating tips of the first and second catheters, showing the receptor, which includes a proximal end, a distal opening, and a channel providing a guide surface, and the piercing tool, which includes a needle and a plug encompassing the catheter adjacent the base of the needle, and showing the contours of the plug, needle, and receptor channel that provide for mating between the tips.

FIG. 10 is a piercing tool for use in a second embodiment of the present invention that includes a base and a needle that is offset from the base by an angle.

FIG. 13 is a cross-sectional view of another aspect of the present disclosure having a plurality of openings.

FIG. 14 is a cross-sectional view of an embodiment similar to that shown in FIG. 13 having a plurality of openings and a resizable portion.

FIG. 15 is a cross-sectional view of the embodiment of FIG. 13 inside the lumen of a first vessel and aimed at a second vessel.

FIG. 16 is a cross-sectional view of two vessels with an embodiment of the present disclosure having an expandable balloon support in an expanded state, with a piercing tool extending from an opening of the catheter, through walls of the first and second vessels, and into the lumen of the second vessel.

DETAILED DESCRIPTION OF THE PREFERRED EMBODIMENTS

Figure 1:
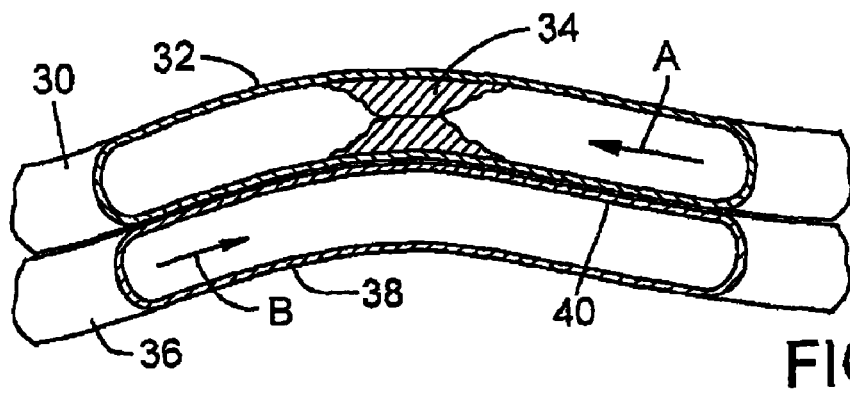
FIG. 1 is a partial cross-sectional view showing an obstructed artery, including the obstruction and the area adjacent both ends of the obstruction, and a vein alongside the artery.

As shown in FIG. 1, an artery 30, formed by an artery wall 32, has a blood flow, indicated by arrow A, that is partially or totally blocked by an obstruction or occlusion 34, typically formed by plaque. A vein 36 roughly similar in dimension to artery 30 lies alongside and generally parallel to artery 30. Vein 36, formed by a vein wall 38, includes, in the area proximal to occlusion 34, a portion 40 in close proximity to artery 30 that the physician has selected as a venous site for creating a fistula between artery 30 and vein 36. The normal blood flow through vein 36 would be in the direction indicated by arrow B.

Figure 2:
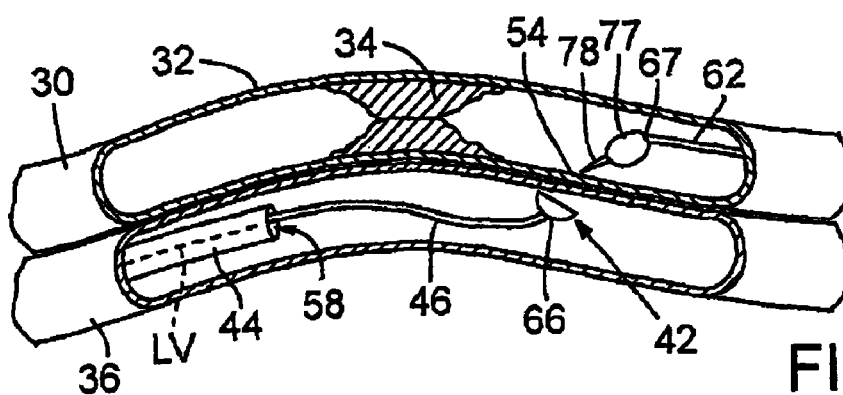
FIG. 2 is a cross-sectional view of an embodiment of the present invention in the blood vessels of FIG. 1 with a first catheter with a distal end inserted into the artery and a second catheter with a distal end inserted into the vein, the catheters carrying at their distal ends mating tips, i.e., a piercing tool on the first catheter and a receptor on the second catheter.

An embodiment of the invented system, indicated generally at 42 in FIG. 2, is a catheter apparatus that includes a first catheter 62 and a second catheter 44. In FIG. 2, the first catheter is in the artery and the second catheter is in the vein, but this can be reversed. Similarly, the first catheter in the artery is shown upstream from occlusion 34, but this may alternatively be reversed to begin the procedure downstream from the occlusion and proceeding afterwards to the upstream side.

Second catheter 44 may include at least one lumen 58 which runs generally parallel to a longitudinal axis LV of catheter 44. A wire 46 may be inserted through lumen 58. Typically, wire 46 has an outer diameter of 0.035-inches, but any suitable dimension may be used. Wire 46 may be controllable by the physician in position relative to catheter 44. Wire 46 may be a guidewire for catheter 44, or a separate guidewire may be used, with other lumens in catheter 44 providing the channel for the separate guidewire.

As shown in FIG. 2, first catheter 62 of catheter apparatus 42 includes a distal end 67 that the physician may insert into artery 30 for positioning adjacent arterial fistula site 54. First catheter 62 may include one or more lumens running generally parallel to a longitudinal axis of catheter 62. First catheter 62 may be guided along a guidewire or may itself be a guidewire, typically with an outer diameter of 0.035-inches, although any suitable dimension may be used. First catheter 62 preferably is hollow.

Figure 3:
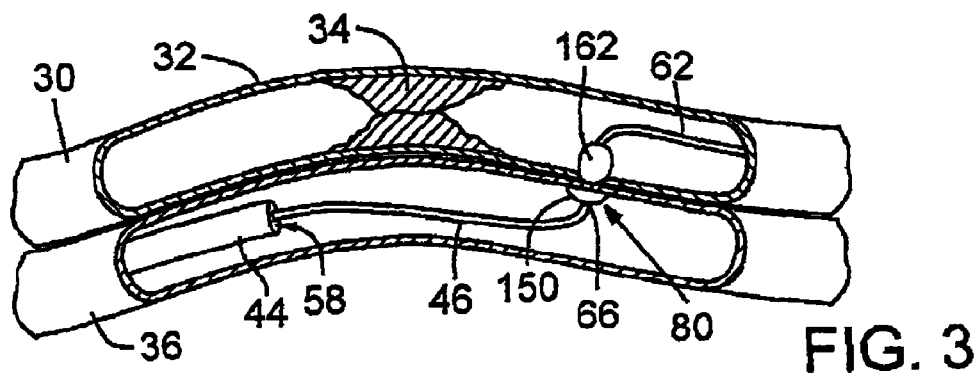
FIG. 3 is a cross-sectional view of the vein, artery, and two catheters, as in FIG. 2 with the tips of the catheters mated to create a pair of co-located openings in the walls of the vein and artery for connection of a fistula between the artery and the vein.

A piercing tool 77 that includes a sharp needle 78 may be selectively deployed, as shown in FIGS. 2 and 3, or withdrawn into the lumen of catheter 62. Needle 78 is preferably withdrawn while catheter 44 is maneuvered to the fistula site so as not to cause trauma to the blood vessel wall.

As best seen in FIG. 9, needle 78 may be disposed at the distal end of a wire 178 disposed in the lumen of catheter 62. The physician can control the positioning of wire 178 and needle 78 relative to catheter 62. Guidewire 46 may include a receptor 150, such as substantially cup-shaped socket 152. Receptor 150 includes a distal opening 154, preferably circular, and a proximal end 156. Receptor 150 includes a channel 158 leading from opening 154 toward proximal end 156. Channel 158 preferably narrows in a direction from opening 154 toward proximal end 156. Channel 158 is defined by an inner surface 160 that provides a guide surface for needle 78 that directs the needle toward proximal end 156 of receptor 150. Channel 158 may be substantially conical, or have such other shape as tends to mate with, and guide piercing tool 77 into receptor 150.

Piercing tool 77 on catheter 62 preferably includes a plug 162 provided with an outer contour that narrows from a proximal end 164 toward a distal end 166. Plug 162 preferably mates with channel 158 in receptor 150. Plug 162 preferably encompasses catheter 62 adjacent the distal end of the catheter. As seen in FIGS. 2, 3, and 9, the piercing tool and the receptor have a complementary configuration that supports their mating together.

Typically, piercing tool 77 will include a magnet with one pole oriented toward the distal end of the tool, while receptor 150 will include a magnet with the opposite pole oriented toward the distal end of the receptor which will draw the needle into the receptor. For example, the magnets may be annular rings or donuts and formed of a strong permanent magnet material suitable for the intended use.

A typical arrangement, shown in FIG. 9, is that plug 162 includes a first magnet 168 generally in a donut shape and having a north pole N positioned distally with respect to a south pole S. Typically magnet 168 is spaced from the distal end of plug 162. A second magnet 170 may be disposed on, or form an integral part of receptor 152, preferably adjacent distal opening 154 of socket 152. Second magnet 170 may be arranged with a south pole S distal of a north pole N to attract magnet 168 when the tips of the two catheters are in proximity, e.g., with each catheter in an adjacent blood vessel. Alternatively or in addition, one or more magnets may be arranged in various locations on plug 162 and/or needle 78 and on or in receptor 150, e.g., adjacent proximal end 156, with the poles arranged to draw piercing tool 77 into receptor 150.

Figure 4:
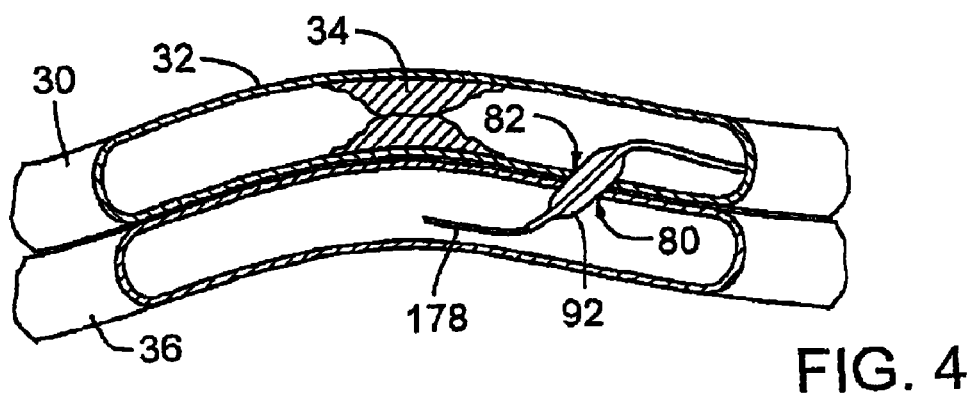
FIG. 4 is a cross-sectional view of the vein and artery with a balloon inserted through both openings.

As shown in FIGS. 3 and 4, after creating openings 80, 82 with a tool such as needle 78, the physician withdraws catheter 62 from the fistula site, leaving wire 178 in place, and a balloon 92 may be inserted over wire 178 and through openings 80, 82 and inflated to enlarge the openings. Balloon 92 may include radiopaque markers and may be inflated with a solution containing a radiopaque dye or contrast to allow the physician to radiographically monitor and adjust the position of the balloon before, during, and after inflation.

Figure 5:
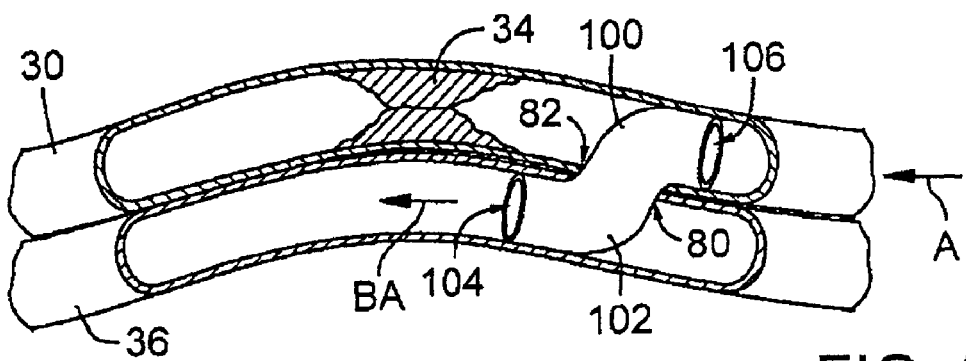
FIG. 5 is a cross-sectional view of the vein and artery with a stent installed through the openings between the vein and artery to maintain a fistula therebetween.

As shown in FIG. 5, a device for maintaining an open, leak-free connection between openings 80 and 82, such as stent 100, is inserted through the openings. Stent 100 includes a frame 102 having two open ends 104 and 106 that preferably create leak-free couplings to the inside of artery 30 and vein 36. With openings 80, 82 connected to form a fistula, vein 36 is arterialized, and blood flows from artery 30 into vein 36 in the direction indicated by arrows A and BA.

Stent 100 is typically a short, covered stent, such as the Hemobahn stent made by WL Gore & Associates.

Figure 6:
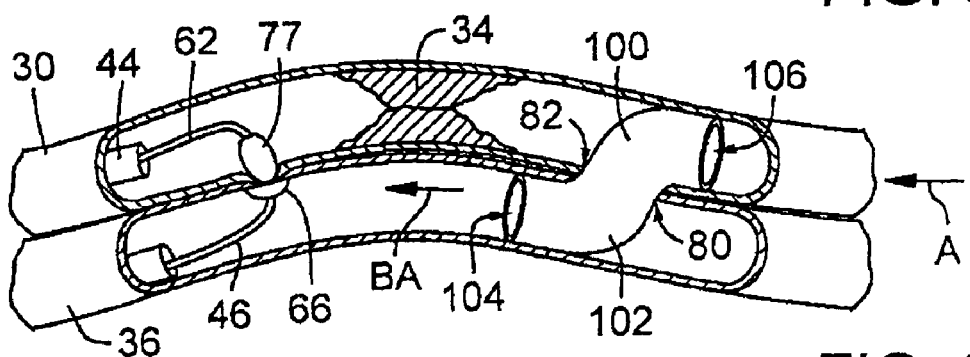
FIG. 6 is a cross-sectional view of a first catheter inserted in the artery and a second catheter inserted in the vein at the other end of the obstruction depicted in FIGS. 1-4, the catheters including mating tips shown in a joined position to create a second pair of co-located openings through the vein and artery walls.
Figure 7:
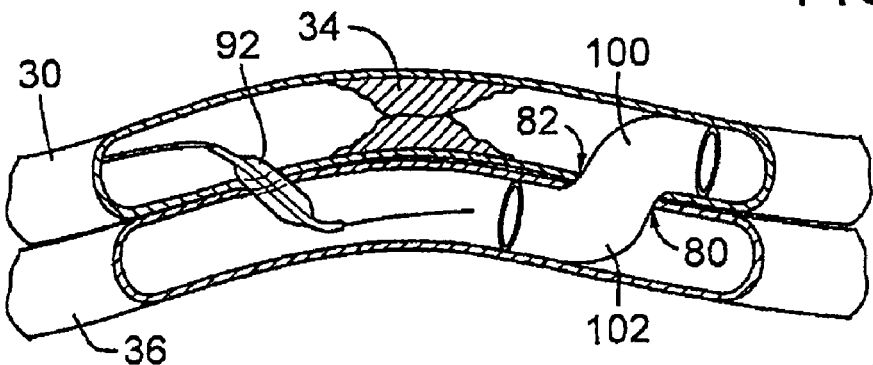
FIG. 7 is a cross-sectional view of the vein and artery with a balloon inserted through the second pair of openings between the vein and the artery.
Figure 8:
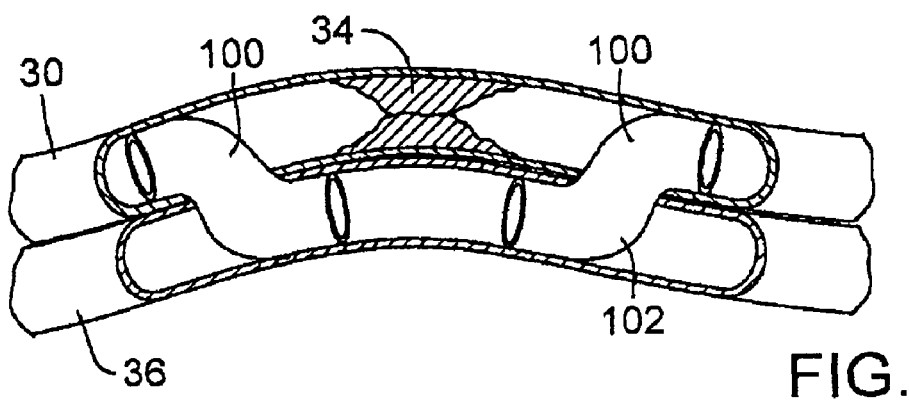
FIG. 8 is a cross-sectional view of the vein and artery with a second stent installed through the second pair of openings between the vein and artery to maintain a fistula therebetween.

As shown in FIGS. 6, 7, and 8 a second pair of co-located openings may be created, and a stented fistula established therebetween, using essentially the same catheter system and method as described for FIGS. 1-5 and 9. FIG. 6 illustrates that the first catheter with the piercing tool preferably is inserted into the artery and the openings created from the artery into the vein. Alternatively, the openings may be created from the vein into the artery.

An alternative embodiment for the piercing tool in shown in FIG. 10. This tool 77a may be used with a metal guidewire 62a that preferably includes a lumen 58a. An inner wire 178a may be inserted in lumen 58a, providing a base for a needle 78a. The coupling between the needle and base incorporates a curvature such that the needle is nominally offset from the base by an angle OA, typically between about 30-degrees and about 90-degrees. Inner wire 178a is typically made of a sufficiently rigid material, such as nitinol and/or stainless steel, as to maintain the offset angle as the needle is used to pierce blood vessels. Guidewire 62a is preferably formed of a sufficiently rigid material such that when needle 78a is retracted into lumen 58a, the curvature between the needle and the base is overcome and the needle temporarily aligns with the base in a non-traumatic configuration. Inner wire 178a may have an outer diameter of 0.010, 0.014, 0.018, or 0.021-inches, or such other dimension as is suited to the particular application.

Figure 11:
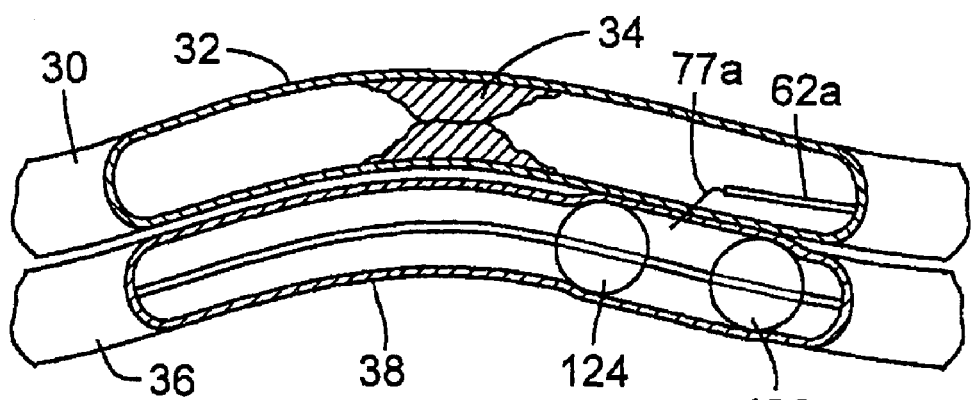
FIG. 11 illustrates the use of the piercing tool of FIG. 10 in conjunction with a double-balloon catheter to create openings in a vein and an artery.

As shown in FIG. 11, piercing tool 77a may be inserted in artery 30, typically while withdrawn into the catheter 62a while maneuvering to the fistula site. Piercing tool 77a may be used in conjunction with a catheter having two balloons 124 and 126 that are inserted in vein 36. In such case, the catheter tips are maneuvered to opposing sides of the proposed fistula site and balloons 124 and 126 are inflated to press the vein wall against the artery wall. Also, fluid may be injected into the sealed-off area to further press the two blood vessel walls together. Then piercing tool 77a is deployed and maneuvered through the artery and then the vein wall to create openings for forming the fistula as for the embodiments described above.

FIG. 11 depicts the piercing tool and the balloon catheter in different vessels. Alternatively, piercing tool 77a may be inserted in the same blood vessel with the balloon catheter. In such an embodiment, the balloons are preferably independently inflatable, and typically the distal balloon 124 is inflated first to stop blood flow. Then, piercing tool 77a is maneuvered to the fistula site in a manner similar to that for the previously described embodiment, typically with the piercing tool withdrawn into the guidewire to the non-traumatic configuration.

With the piercing tool at the fistula site, the proximal balloon 126 is inflated to seal off the fistula site and also to press the vein against the artery. Then, piercing tool 77a is deployed at the end of guidewire 62a and maneuvered by the physician to create the openings from one blood vessel, through both walls, to the other blood vessel.

In either case, piercing tool 77a may be used to create multiple pairs of co-located openings which are then stented to arterialize a portion of the vein to bypass a blockage using a similar method as described above for the embodiment of FIGS. 1-9.

Figure 12:
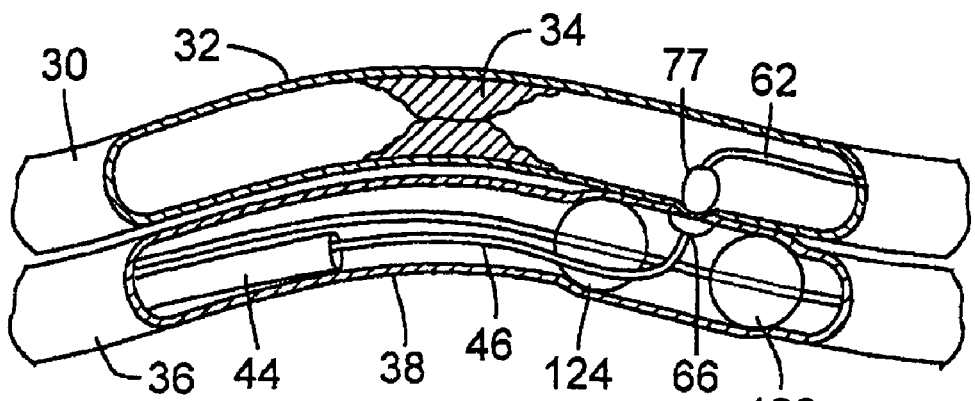
FIG. 12 illustrates the use of the piercing tool of FIGS. 2, 3, 6, and 9 in conjunction with a double-balloon catheter to create openings in a vein and an artery.

As shown in FIG. 12, the double balloon catheter may also be used in conjunction with the catheters 44 and 62 that include the mating tips. In this embodiment, the double balloon catheter helps to control blood flow at the planned fistula site and to press the blood vessel walls together to assist in the mating of the tips. The fistula creation otherwise proceeds in a similar manner as for the embodiment of FIGS. 1-9.

FIG. 13 depicts another aspect of the disclosure directed towards a catheter 230 having an outer surface 232, a distal end 234, a first lumen 236 (not shown), and a plurality of openings 240.

FIG. 14 shows a alternative catheter 230 according to the present disclosure, the catheter 230 having the same features of the catheter in FIG. 13, except this catheter 230 has a resizable portion 250 disposed on its outer surface, and an arc of its surface 252 which is unobstructed by the resizable portion 250.

Figure 17:
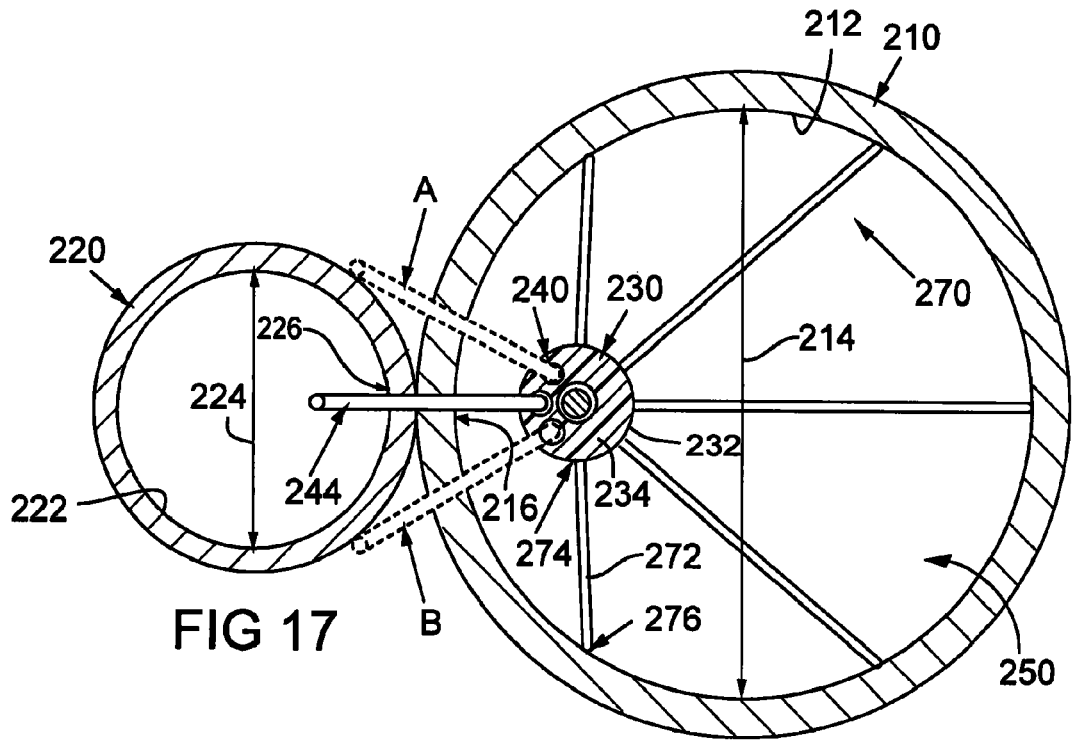
FIG. 17 is a cross-sectional view of the two vessels and an embodiment of this disclosure with pivotable members stabilizing it inside the lumen of the first vessel, where a physician has twice attempted unsuccessfully to traverse from the first vessel to the second vessel, and has succeeded in a third attempt.
Figure 18:
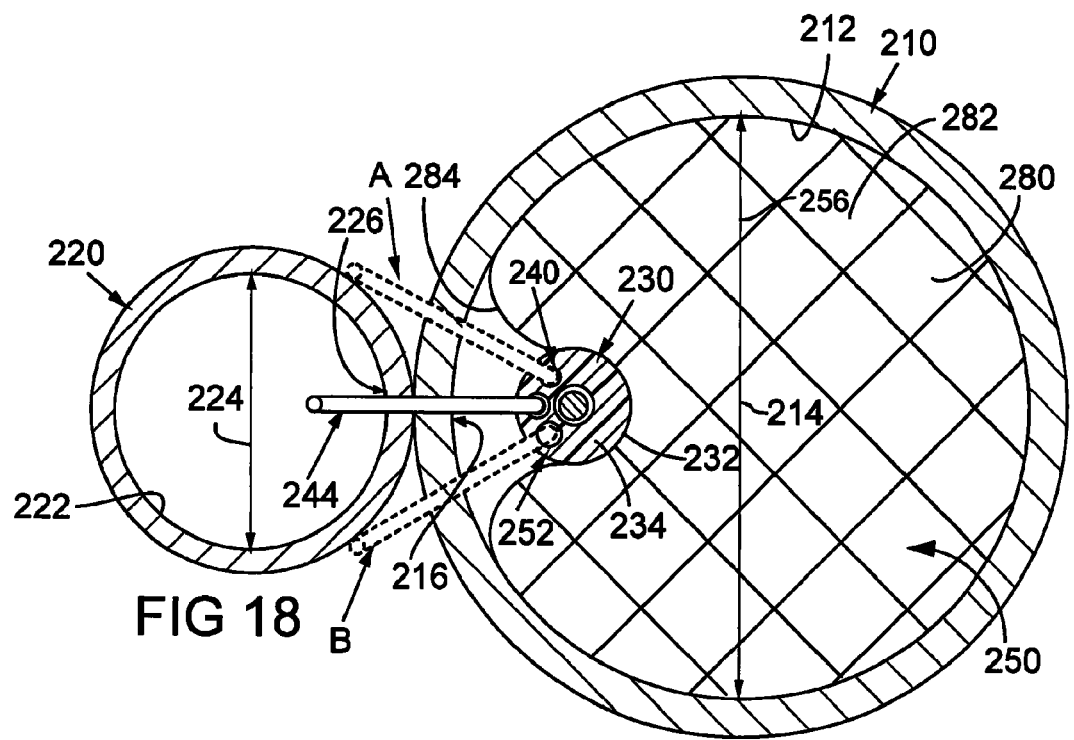
FIG. 18 is a cross-sectional view of the two vessels and an embodiment of this disclosure with an expandable stent stabilizing it inside the lumen of the first vessel, where a physician has twice attempted unsuccessfully to traverse from the first vessel to the second vessel, and has succeeded in a third attempt.

FIG. 15 shows a first vessel 210, formed by a vessel wall 212 and having a first diameter 214, with a first portion 216 intended for an opening or a fistula. A second vessel 220 lies alongside and generally parallel to first vessel 210. Second vessel 220, formed by a second vessel wall 222 and having a second diameter 224, includes a second portion 226, in the second vessel wall 222 in close proximity to the first portion 216 of the first vessel wall 212, that a physician may select as a site for creating a fistula between first vessel 210 and second vessel 220. In this particular example, the first diameter 214 is substantially similar to the second diameter 224. However, as seen in FIGS. 16-18, the first diameter 214 may also be substantially larger than the second diameter 224, which would typically be the case if the first vessel 210 is a vein, and the second vessel 220 is an artery. A catheter system of the present disclosure may be used in any of the above scenarios.

A catheter 230 similar to the one depicted in FIG. 13 is seen inside the lumen of the first vessel 210 in FIG. 15. The plurality of openings 240 are seen pointed generally towards the second vessel 220.

FIG. 16 shows a view where the first diameter 214 is greater than the second diameter 224. In this figure a piecing tool 244 is seen extending from one of the openings 240 in the catheter 230, through the first vessel wall 212 at the portion intended for a fistula 216, through the second vessel wall 222 at the second portion intended for fistula 226, and into the lumen of the second vessel 220. Also shown is a resizable portion 250 disposed on the outer surface 232 of the catheter 230, which will be described in greater detail below.

While the openings 240 are shown in the figures as comprising three openings, it should be understood that any number of openings may be disposed in the outer surface 232 or on the distal end 234 of the catheter 230. Further, while the openings 240 are shown generally defining an arc which subtends an angle less than 360° of the catheter 230 circumference, it is possible that the openings 240 may define any arc on the catheter 230, including the entire circumference of the catheter 230. In the preferred embodiment, the angle subtended by the arc created by the openings 240 is between 0° and 180°.

FIGS. 17 and 18 show similar views. In both figures, the physician has made first and second unsuccessful attempts (denoted 'A' and 'B') to create a fistula between the first vessel 210 and the second vessel 220 using a piercing tool 244, followed by a successful attempt in which the piercing tool 244 has pierced the first vessel wall 212 and the second vessel wall 222 and has extended into the lumen of the second vessel 220.

The piercing tool 244 may be rotated within the catheter 230 without rotating the catheter 230. In this arrangement, a physician may fire the piercing tool 244 through any of the openings 240, giving the physician a wide arc of potential space through which the piercing tool 244 may be fired. Such an arc enables the physician to avoid rotating the catheter 230 any more than necessary, minimizing possible damage to the first vessel 210.

The piercing tool 244 may be selectively deployed, as shown in FIGS. 16-20, or withdrawn into the first lumen of catheter 230. The piercing tool 244 is preferably withdrawn while catheter 230 is maneuvered to the fistula site so as not to cause trauma to the blood vessel wall. The piercing tool 244 may come in numerous varieties, including but not limited to the instruments recited in U.S. Pat. No. 6,464,665, as well as the catheter systems described above.

Figure 19:
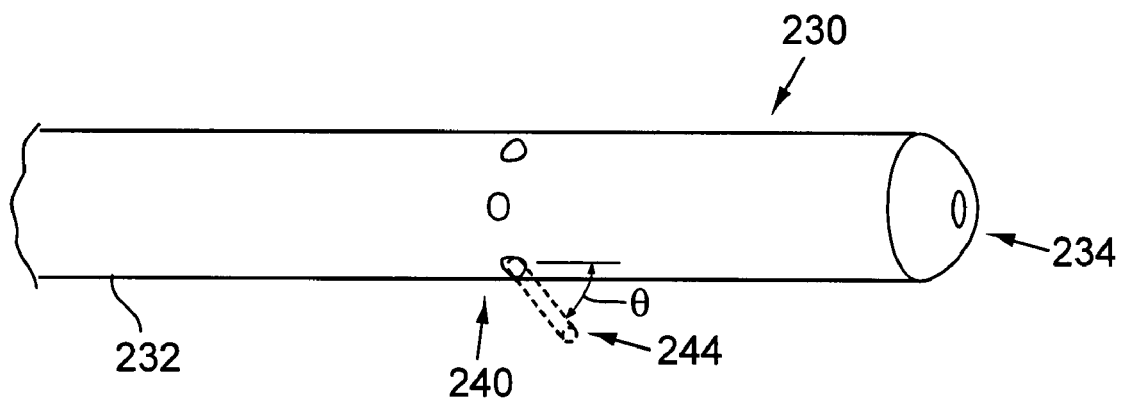
FIG. 19 shows one possible arrangement of the plurality of openings on the catheter.
Figure 20:
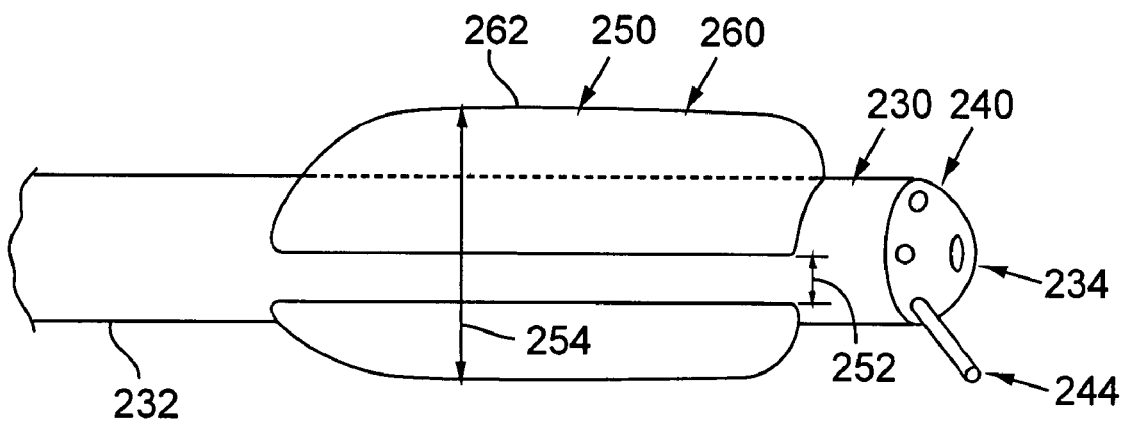
FIG. 20 shows another possible arrangement of the plurality of openings on the catheter.

FIGS. 19 and 20 depict alternative embodiments of how the piercing tool 244 may be extended. As depicted in FIG. 19, the openings 240 may be disposed on the outer surface 232 of the catheter 230 on a side portion of the catheter. In this embodiment, the piercing tool 244 may exit the catheter 230 at an angle θ to the longitudinal pole of the catheter 230. θ may be any angle between 0° and 90°.

In FIG. 20, the piercing tool 244 may extend from any one of the plurality of openings 240 which are disposed on the distal end 234 of the catheter 230. In this embodiment, the piercing tool 244 may exit the catheter 230 at any angle from perpendicular to the longitudinal axis of the catheter 230 to substantially parallel to the longitudinal axis.

The resizable portion 250 may surround any portion of the outer surface 232 of the catheter. In an exemplary embodiment, the resizable portion 250 may surround less than the whole arc of the surface 232. The arc (or arcs) of the surface not surrounded by the resizable portion 250, hereafter known as the free arc(s) 252, may provide an unobstructed pathway for a piercing tool 244 to traverse. Thus, free arc 252 must be large enough to accommodate a piercing tool 244 extending from any of the plurality of openings 240, as seen best in FIGS. 16 and 18.

The resizable portion 250 may have a nominal configuration and an active configuration. In the nominal configuration, the resizable portion may have a nominal diameter 254 (seen in FIGS. 14 and 20). In the active configuration the resizable portion 250 may have an active diameter 256, which may be greater than the nominal diameter 254 (seen in FIGS. 14 and 20).

The resizable portion 250 may be completely or partially radiopaque, so that a physician can view and adjust the position of the free arc 252, and hence control the direction which the piercing tool 244 will fire. In one embodiment, the resizable portion 250 is independently rotatable within a vessel. As seen best in FIGS. 16 and 18, the resizable portion 250 is aligned so that the free arc 252 faces the portion intended for the fistula 216 and the second vessel 220.

The resizable portion 250 is shown in the active configuration having an active diameter 256 in FIG. 16. The active diameter 256 may be substantially equal to the first diameter 214 of the first vessel 210. It should be understood that having an active diameter 256 substantially equal to the first diameter of the first vessel will cause the resizable portion 250 to stabilize the catheter 230 within the first vessel 210.

Some embodiments of the resizable portion 250 may hold the catheter 230 in the center of the first vessel 210. Other embodiments may hold the catheter 230 against a site intended for an opening 216 of a vessel wall 212, or somewhat spaced from such a site 216.

In one embodiment of the disclosure, depicted in FIGS. 14, 16 and 20, the resizable portion 250 is a balloon 260 having a nominal configuration and an active configuration. In such an embodiment, catheter 230 may include a second lumen 238 used to inflate the balloon 260.

In the nominal configuration (seen in FIG. 14), the balloon 260 is deflated with a nominal diameter 254 which is less than the first diameter 214 (seen in FIGS. 15-18) of the first vessel 210. In the active configuration, the balloon 260 may be inflated to an active diameter 256. The active diameter 256 may be of any size greater than the nominal diameter 254 that will hold the catheter 230 stable in the first vessel 210 by causing the balloon surface 262 to contact the wall 212 of the vessel 210, including but not limited to equal to the diameter 214 of the vessel 210, slightly larger than the diameter 214 of vessel 210, or even slightly smaller than the diameter 214 of the first vessel 210.

Balloon 260 may include radiopaque markers and/or may be inflated with a solution containing a radiopaque dye or contrast to allow the physician to radiographically monitor and adjust the position of the balloon 260 before, during, and after inflation.

In another embodiment, depicted in FIG. 17, catheter 230 has a resizable portion 250 comprising a plurality of retractable members 270. Each retractable member 272 has a proximal end 274 pivotally coupled to the outer surface 232 and a free distal end 276. In the nominal configuration, each retractable member 272 is retracted so that the distal end 276 is in close proximity with the outer surface 232, allowing for easy movement of the catheter 230 through the first vessel 210. In the active configuration, each retractable member 272 is extended so that the distal end 276 is extended away from the outer surface 232 and abutting the first vessel wall 212.

In some embodiments, some retractable members 270 may be longer than others, as shown in FIG. 17. In particular, all the retractable members 270 disposed on a particular portion of the outer surface 232 may be longer or shorter than the retractable members 270 disposed on a different portion of the outer surface. Such differences in length cause the catheter 230 to be held in a position that is offset from the center of the first vessel 210.

In another embodiment, depicted in FIG. 18, catheter 230 has a resizable portion 250 comprising an expandable stent 280 made of stent cells 282 and having an outer surface 284. The stent 280 may be constructed out of any suitable material. In one embodiment, the stent 280 may be metallic. In another embodiment, the stent 280 is at least partially comprised of self-expanding nitinol.

In the nominal configuration, the stent 280 is retracted to a diameter 254 which is less than the first diameter of the first vessel 210, allowing for easy movement of the catheter 230 through the first vessel 210. In the active configuration, the 280 stent is expanded to a diameter 256 substantially equal to the first diameter 214 of the first vessel 210 so that the outer surface 284 of the stent abuts the first vessel wall 212. The diameter 256 in the active configuration may be of any size that will hold the catheter 230 stable in the vessel 210 by causing the outer stent surface 284 to abut the first wall 212 of the vessel 210, including but not limited to equal to the first diameter 214 of the vessel 210, slightly larger than the first diameter 214, or even slightly smaller than the first diameter 214.

It is believed that the following claims particularly point out certain combinations and subcombinations that are directed to one of the disclosed disclosures and are novel and non-obvious. Disclosures embodied in other combinations and subcombinations of features, functions, elements and/or properties may be claimed through amendment of the present claims or presentation of new claims in this or a related application. Such amended or new claims, whether they are directed to a different disclosure or directed to the same disclosure, whether different, broader, narrower or equal in scope to the original claims, are also included within the subject matter of the disclosures of the present disclosure.

We claim:

1. A catheter system for piercing a first wall of a first blood vessel and a second wall of a second blood vessel to create a fistula between the blood vessels, the system comprising:
   a catheter having a tubular wall with an outer surface, a first lumen and a distal end insertable to a position wherein the distal end is adjacent a site within the first blood vessel for the fistula;
   a piercing tool for creating the fistula, the piercing tool disposed within and extendable from the first lumen;
   a first opening through the tubular wall and configured to receive the piercing tool from the lumen and direct it outwardly in a first direction relative to the catheter; and
   a second opening through the tubular wall and circumferentially aligned with the first opening, said second opening configured to receive the piercing tool from the lumen and direct it outwardly in a second direction relative to the catheter, the second direction being different from the first direction.

2. The catheter system of claim 1, wherein the first and second openings are disposed on the outer surface adjacent to the distal end.

3. The catheter system of claim 1, wherein the first and second openings are disposed on the distal end.

4. The catheter system of claim 1, further comprising a third opening configured to receive the piercing tool from the lumen and direct it outwardly in a third direction relative to the catheter, wherein the third direction is different than both the first direction and the second direction.

5. The catheter system of claim 1, further comprising a resizable portion for stabilizing the catheter within the first blood vessel, the resizable portion disposed on the outer surface adjacent to the distal end so that a first arc of the outer surface is unobstructed by the resizable portion, the resizable portion being manipulable between a nominal configuration and an active configuration, the nominal configuration having a diameter less than the diameter of the first vessel, and the active configuration having a diameter substantially equal to the diameter of the first vessel.

6. The catheter system of claim 5, wherein the resizable portion is a balloon, and the catheter includes a second lumen configured to inflate the balloon.

7. The catheter system of claim 5, the resizable portion comprising three or more retractable members with proximal ends and distal ends, each member being coupled at its proximal end to the outer surface and free at its distal end, whereby the distal ends are in close proximity with the outer surface in the nominal configuration and extended away from the outer surface in the active configuration.

8. The catheter system of claim 7, wherein the members contain metal.

9. The catheter system of claim 7, wherein the members contain nitinol.

10. The catheter system of claim 5, the resizable portion comprising a stent wherein the stent in the nominal configuration is retracted and the stent in the active configuration is expanded.

11. The catheter system of claim 10, wherein the stent is metallic.

12. The catheter system of claim 10, wherein the stent contains nitinol.

13. A catheter system for piercing a first wall of a first blood vessel and a second wall of a second blood vessel to create a fistula between the blood vessels, the system comprising:
   a first catheter having a tubular wall with a distal end insertable to a position wherein the distal end is adjacent a site within the first blood vessel for the fistula, an outer surface, a lumen, a piercing tool adjacent the distal end and disposed within the lumen, a first opening through the tubular wall and configured to receive the piercing tool from the lumen and direct it outwardly in a first direction relative to the first catheter, and a second opening through the tubular wall and circumferentially aligned with the first opening, said second opening configured to receive the piercing tool from the lumen and direct it outwardly in a second direction relative to the first catheter, wherein the second direction is different than the first direction;
   a second catheter having a distal end insertable to a position wherein the distal end is adjacent a site within the second blood vessel for the fistula, the second catheter including adjacent the distal end a receptor having a distal opening and a proximal end, the receptor further including a channel leading from the opening toward the proximal end; and one or more magnets disposed on at least one of the catheters to draw the piercing tool into the channel of the receptor.

14. The catheter system of claim 13, wherein the first and second openings are disposed on the outer surface of the first catheter adjacent to the distal end.

15. The catheter system of claim 13, wherein the first and second openings are disposed on the distal end of the first catheter.

16. The catheter system of claim 13, further comprising a third opening configured to receive the piercing tool from the lumen and direct it outwardly in a third direction relative to the first catheter, wherein the third direction is different than both the first direction and the second direction.

17. The catheter system of claim 13, further comprising a resizable portion for stabilizing the first catheter within the first blood vessel, the resizable portion disposed on the outer surface of the first catheter adjacent to the distal end so that a first arc of the outer surface is unobstructed by the resizable portion, the resizable portion being manipulable between a nominal configuration and an active configuration, the nominal configuration having a diameter less than the diameter of the first blood vessel, and the active configuration having a diameter substantially equal to the diameter of the first blood vessel.

18. The catheter system of claim 17, wherein the resizable portion is a balloon, and the first catheter includes a second lumen configured to inflate the balloon.

19. The catheter system of claim 17, the resizable portion comprising three or more retractable members with proximal ends and distal ends, each member being coupled at its proximal end to the outer surface of the first catheter and free at its distal end, whereby the distal ends are in close proximity with the outer surface in the nominal configuration and extended away from the outer surface in the active configuration.

20. The catheter system of claim 19, wherein the members contain metal.

21. The catheter system of claim 19, wherein the members contain nitinol.

22. The catheter system of claim 19, the resizable portion comprising a stent wherein the stent in the nominal configuration is retracted and the stent in the active configuration is expanded.

23. The catheter system of claim 22, wherein the stent is metallic.

24. The catheter system of claim 22, wherein the stent contains nitinol.

* * * * *